(12) United States Patent
Romeo

(10) Patent No.: US 10,929,939 B2
(45) Date of Patent: Feb. 23, 2021

(54) BUSINESS INTELLIGENCE PORTAL

(71) Applicant: Breg, Inc., Carlsbad, CA (US)

(72) Inventor: Steven Robert Romeo, Encinitas, CA (US)

(73) Assignee: Breg, Inc., Carlsbad, CA (US)

( * ) Notice: Subject to any disclaimer, the term of this patent is extended or adjusted under 35 U.S.C. 154(b) by 141 days.

(21) Appl. No.: 14/216,657

(22) Filed: Mar. 17, 2014

(65) Prior Publication Data
US 2018/0165780 A1   Jun. 14, 2018

Related U.S. Application Data

(60) Provisional application No. 61/800,181, filed on Mar. 15, 2013.

(51) Int. Cl.
G06Q 50/22 (2018.01)
G06Q 10/06 (2012.01)
G16H 20/30 (2018.01)

(52) U.S. Cl.
CPC ....... G06Q 50/22 (2013.01); G06Q 10/06375 (2013.01); G16H 20/30 (2018.01)

(58) Field of Classification Search
None
See application file for complete search history.

(56) References Cited

U.S. PATENT DOCUMENTS

| | | | | |
|---|---|---|---|---|
| 7,191,183 B1 * | 3/2007 | Goldstein | ......... | G06F 17/30893 705/2 |
| 7,389,245 B1 * | 6/2008 | Ashford | ................. | G06Q 30/02 705/14.34 |
| 7,689,439 B2 * | 3/2010 | Parker | ................... | G06F 19/363 600/300 |
| 2003/0078813 A1 * | 4/2003 | Haskell | ................. | G06F 19/325 705/3 |
| 2005/0102158 A1 * | 5/2005 | Maeda | ................... | G06Q 50/22 705/2 |
| 2005/0182655 A1 * | 8/2005 | Merzlak | ................. | G06Q 50/24 705/2 |
| 2006/0106646 A1 * | 5/2006 | Squilla | ............... | G06F 19/3418 705/3 |
| 2006/0109961 A1 * | 5/2006 | Mahesh | ................. | G06Q 10/06 379/93.25 |
| 2006/0122981 A1 * | 6/2006 | Jennery | ............ | G06F 17/30507 |
| 2006/0155581 A1 * | 7/2006 | Eisenberger | ........ | G06F 17/3089 705/3 |
| 2006/0218010 A1 * | 9/2006 | Michon | ................. | G06F 19/345 705/3 |
| 2008/0082357 A1 * | 4/2008 | Schmitt | ................... | G06Q 10/10 705/2 |
| 2008/0091471 A1 * | 4/2008 | Michon | ............... | G06F 19/3443 705/3 |

(Continued)

Primary Examiner — Rachelle L Reichert
(74) Attorney, Agent, or Firm — Thomas A. Runk; Brooks Kushman P.C.

(57) ABSTRACT

Systems and methods are provided for pulling clinical data associated with a clinic or healthcare practice. The pulled clinical data can be analyzed and/or compared to other clinical data, such as industry clinical data, and subsequently displayed to a user. Additionally, the pulled clinical data can be analyzed so as to determine and generate one or more suggestive actions for improving the efficiency and/or finances of the clinic or healthcare practice in the context of business workflow management.

2 Claims, 10 Drawing Sheets

(56) References Cited

U.S. PATENT DOCUMENTS

| | | | |
|---|---|---|---|
| 2008/0172249 A1* | 7/2008 | Glaser-Seidnitzer | G06Q 50/22 705/2 |
| 2008/0215370 A1* | 9/2008 | Dent | G06F 19/3487 705/3 |
| 2008/0256128 A1* | 10/2008 | Pierce | G06F 19/363 |
| 2009/0012811 A1* | 1/2009 | Haider | G06Q 50/22 705/2 |
| 2009/0037225 A1* | 2/2009 | Burchianti, II | G06F 19/327 705/3 |
| 2009/0070149 A1* | 3/2009 | Kurian | G06Q 50/24 705/3 |
| 2009/0076841 A1* | 3/2009 | Baker | G06F 19/327 705/2 |
| 2009/0299767 A1* | 12/2009 | Michon | G06F 19/3443 705/3 |
| 2011/0077973 A1* | 3/2011 | Breitenstein | G06Q 10/10 705/3 |
| 2011/0117528 A1* | 5/2011 | Marciello | G06F 19/3437 434/262 |
| 2011/0246236 A1* | 10/2011 | Green, III | G06F 19/328 705/3 |
| 2011/0301982 A1* | 12/2011 | Green, Jr. | G06F 19/3443 705/3 |
| 2012/0215560 A1* | 8/2012 | Ofek | G06F 19/322 705/3 |
| 2012/0232919 A1* | 9/2012 | Wilson | G06F 19/345 705/2 |
| 2012/0259661 A1* | 10/2012 | Walker | G06F 17/2247 705/3 |
| 2012/0310667 A1* | 12/2012 | Altman | G06F 19/325 705/3 |
| 2013/0123667 A1* | 5/2013 | Komatireddy | A61B 5/0002 600/595 |
| 2013/0290005 A1* | 10/2013 | Vesto | G06Q 10/06 705/2 |
| 2014/0081661 A1* | 3/2014 | Fu | G06F 19/3481 705/3 |

* cited by examiner

| ACTION 300 | OUTCOME 310 |
|---|---|
| PULL BILLED DOLLARS AND RECEIVED AR FROM BILLING AND ERP SYSTEMS 301 | UNIFY DISPENSMENT DATA TO VISUALIZE BILLED DOLLARS 311 |
| PULL EACH CLINIC LOCATION 302 | EVALUATE PRODUCT MIX FOR EACH LOCATION AND PRODUCT RUN 312 |
| PULL DATA FROM THE SCHEDULING SYSTEM AND EMR 303 | EVALUATE EFFICIENCY AND PROCESS 313 |
| PULL EMR DATA RECORD AROUND PATIENT CARE AND RECOVERY CYCLES 304 | EVALUATE OUTCOMES AND EFFECTIVENESS OF PRODUCT USE AGAINST EACH CODE 314 |
| REVIEW ORDER CYCLES AND SHIPPING CHARGES 305 | PROVIDE INTELLIGENCE ON HOW TO BULK ORDER AND/OR MODIFY PAR LEVELS 315 |
| PULL PHYSICIAN NOTES FROM EMR AND LINK THE DATA TO PRODUCT USE AND TO PT SYSTEM 306 | DEMONSTRATE OUTCOME ANALYTICS AND A WAY OF IMPROVING OUTCOMES WITH THE DATA PROVIDED 316 |

Fig. 6

BUSINESS INTELLIGENCE PORTAL

CROSS-REFERENCE TO RELATED APPLICATIONS

This application claims the benefit of U.S. Provisional Patent Application Ser. No. 61/800,181 filed Mar. 15, 2013, which is incorporated herein by reference in its entirety.

TECHNICAL FIELD

The disclosed technology relates generally to the healthcare industry, and more particularly, some embodiments relate to a business intelligence application for reporting clinical data for business performance, trending, and suggestive action on the data provided in the clinic.

DESCRIPTION OF THE RELATED ART

While computers and computerized systems have found their way into most of today's businesses, some sectors are more automated than others. For example, certain sectors of the healthcare industry have been slow to automate their systems and procedures, or have yet to evolve into an integrated, user-friendly computerized solution. This is true, for example, with a number of small healthcare practices, family practices, and hospital systems in this country and around the world. However, this shortcoming is not unique to small healthcare practices and indeed, many large healthcare practices suffer from a lack of automation and record-keeping with various aspects of the practice. For example, some computerized systems in use today generate multiple system-to-patient interactions, using different data management systems each having different interfaces to the healthcare provider and the patient.

Additionally, the healthcare industry is in the midst of a paradigm shift with respect to providing services and billing for those services. Previously, healthcare providers have followed a "fee-for-service" model, in which patients are billed according to the individual services given or provided to them, and payers reimburse for those services, regardless of the success of those services. However, the healthcare industry is experiencing a trend of moving away from the fee-for-service model to a "value over volume" or "paying for performance" model. One example of this new model can be referred to as an "episodic" or "bundled" payment model, where a provider (e.g., healthcare practitioner) is given a single, lump sum payment that should cover the expected costs a patient will incur for a particular episode of care. Another example can be referred to as a "partial capitalization" model, where a provider is given a per patient fee, and still another example can be referred to as a "shared savings" model, whereby providers can be financially rewarded for coming under a yearly spending goal.

BRIEF SUMMARY OF EMBODIMENTS

In accordance with one embodiment, a non-transitory computer readable medium comprises executable instructions, the executable instructions being executable by a processor in a client computing device to perform a method, the method comprising obtaining clinical data associated with a clinic from a data repository in accordance with a specified business rule. The method further comprises analyzing the clinical data based on the specified business rule to determine at least one suggestive action for improving business management of the clinic. Additionally, the method comprises displaying the at least one suggestive action in the context of a workflow In accordance with another embodiment, a system for improving business workflow management of a clinic comprises a clinical data management system for obtaining clinical data associated with a clinic from a data repository in accordance with a specified business rule. The clinical data management system is further configured to analyze the clinical data based on the specified business rule to determine a suggestive action for improving business management of the clinic. The system further comprises a device communicatively connected to the clinical data management system, wherein the device hosts an application configured to facilitate displaying the suggestive action in the context of a workflow.

Other features and aspects of the disclosed technology will become apparent from the following detailed description, taken in conjunction with the accompanying drawings, which illustrate, by way of example, the features in accordance with embodiments of the disclosed technology. The summary is not intended to limit the scope of any inventions described herein, which are defined solely by the claims attached hereto.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

FIG. 6 illustrates examples of business rules applied in accordance with one embodiment of the technology described herein.

The figures are not intended to be exhaustive or to limit the invention to the precise form disclosed. It should be understood that the invention can be practiced with modification and alteration, and that the disclosed technology be limited only by the claims and the equivalents thereof.

DETAILED DESCRIPTION OF THE EMBODIMENTS

As alluded to above, the healthcare industry is experiencing a shift in the way services are provided and billed to patients. Given the afore-mentioned emerging models, providers are encouraged to be efficient and reduce/eliminate unnecessary procedures (thereby reducing the cost to treat a patient) while still achieving a good/positive outcome for the patient. However, existing tools for clinical workflow management, particularly in the orthopedic space, are lacking or altogether nonexistent with respect to business workflow management. For example, and similar to the above-described scenarios, orthopedic clinics and practitioners must often manage large amounts of accumulated documentation and/or gather information from incompatible electronic systems lacking a middleware interface, not to mention remain profitable despite rising costs associated with orthopedic practice.

Therefore, business intelligence technology is disclosed herein for efficiently managing a healthcare practice, reducing costs, identifying areas for improvement, and making suggestions to realize such improvements. In particular, a business intelligence portal that may work in conjunction with a business intelligence application is disclosed for obtaining and reporting clinical data for analysis with respect to business performance and patient outcomes/successful treatment, industry trending and comparative analysis, and suggestive action based on the clinical data.

Figure 1:
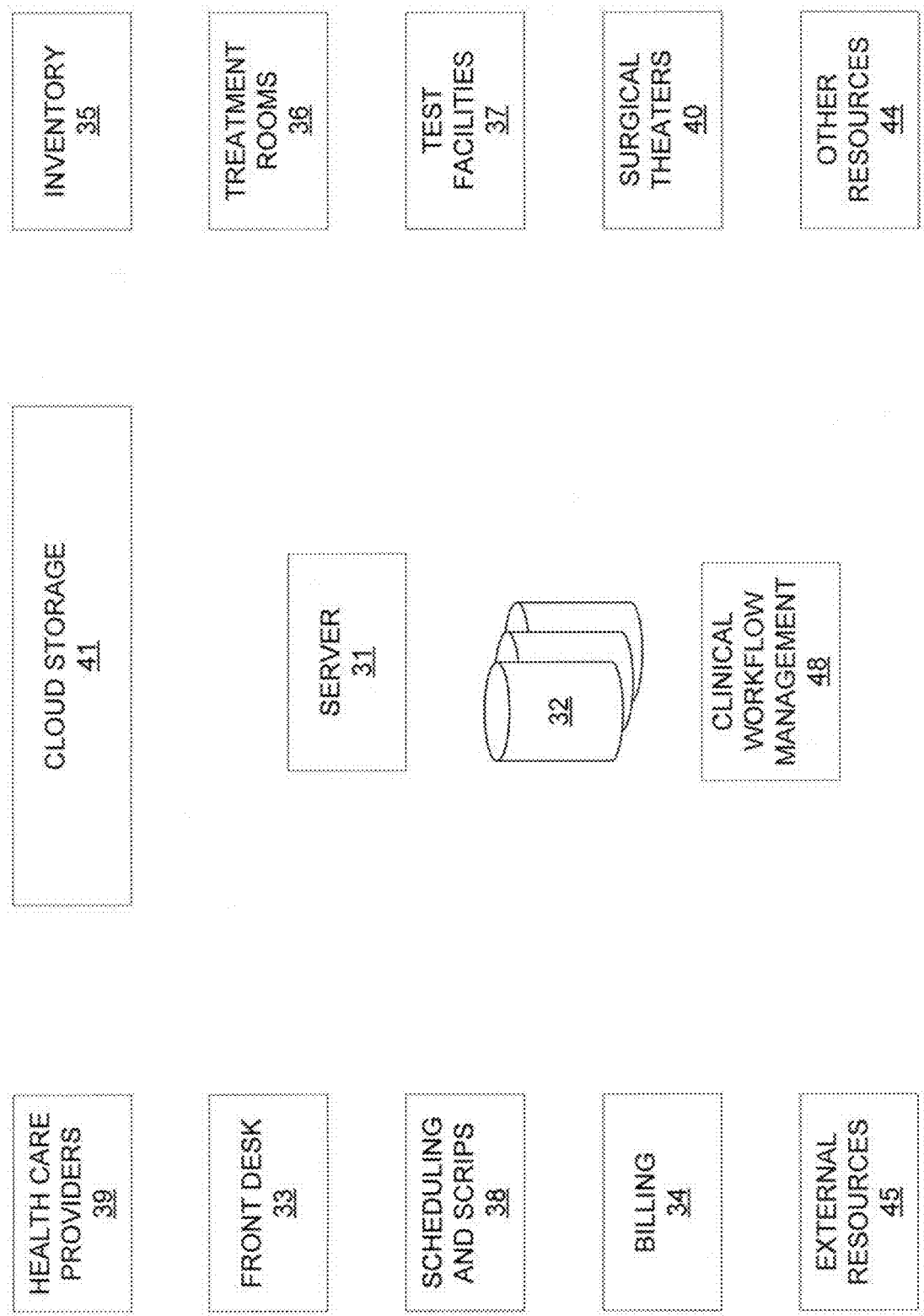
FIG. 1 is a diagram illustrating an example of a healthcare practice in which the disclosed technology may be implemented in accordance with one embodiment of the technology described herein.

Before describing the technology in detail, it is useful to describe an example environment in which the technology can be implemented. One such example is that of the aforementioned clinic or healthcare practice. FIG. 1 is a diagram illustrating an example of a clinic or healthcare practice with which the disclosed technology may be implemented. As used herein, the term "clinic" or "healthcare practice" may be used interchangeably, and can refer to a clinic, hospital, family, or other type of healthcare practice. A clinic or healthcare practice may have one or more medical facilities such as, for example, an orthopedic medicine facility, a sports medicine facility, a pediatric facility and so on. The one or more medical facilities can include physicians, physician assistants, nurse practitioners, radiologists, physical therapists and other healthcare professionals. Moreover, each clinic may include a billing department, inventory, treatment rooms, test facilities, scheduling and prescriptions, one or more surgical theaters, internal resources, etc. Each clinic may rely on the operation of a variety of third party systems such an electronic health records (EHR) system, billing system, and scheduling system.

With reference to FIG. 1, an exemplary clinic or healthcare practice can include one or more of a server 31, server data storage 32, a front desk 33, and a billing department 34, inventory 35, treatment rooms 36, test facilities 37, scheduling and prescriptions 38, one or more healthcare providers 39, one or more surgical theaters were operating rooms 40, cloud data storage 41, and other internal resources 44 and external resources 45.

Server 31 and its associated data storage 32 can be centralized or distributed, and can be configured to store any of a number of different types of data for the healthcare practice. This can include, for example, data such as patient records, including EHR; scheduling information; billing information; and other information and records used in the management, operation and maintenance of the healthcare practice. In addition to data storage 32, each of the other resource units in the healthcare practice can include its own computing and data storage capabilities. In addition to or in place of data storage 32 (and other data storage capabilities) cloud storage 41 can be provided to store data and information used in the healthcare practice. Cloud storage 41 can be configured to be accessible by server 31 as well as by other computing capabilities of the healthcare practice. Although one server 31 is illustrated, as would be apparent to one of ordinary skill in the art after reading this description, a number of different servers 31 can be provided in various logical and physical groupings.

Front desk 33 can be provided to greet and check-in patients at a clinic or healthcare facility. Depending on the size of the healthcare facility, front desk 33 may also be responsible for the functions of billing 34 and scheduling 38 as well as inventory 35. Billing 34 receives information regarding a patient visit, receives insurance and payment information from the patient, generates billing statements, records payments and tracks Accounts Receivable. The information regarding the patient visit used by billing 34 can include information such as, for example, the doctor or healthcare provider visited by the patient, supplies provided to or used in the treatment of the patient, articles delivered to the patient (e.g., a knee brace, crutches, etc.) and other information used to generate the bill. Inventory 35 can include supplies and other inventory used in the operation of the healthcare practice including inventory used in the treatment of patients. For example, in the case of an orthopedic practice, the inventory may include various elbow, knee, and other braces that may be provided or prescribed to a patient. The inventory may also include all other inventory (including consumables) used by the healthcare practice. Inventory levels can be tracked and managed electronically and the reordering of supplies can be automated. Scheduling and prescriptions 38 can be included to provide assistance with scheduling patient visits such as, for example, follow-on appointments, tests, and other events. Scheduling and prescriptions 38 can also manage patient prescriptions, which can include interfacing with pharmacies or other like fulfillment providers.

The healthcare practice generally includes one or more healthcare providers 39 to provide treatment and other services to the patients. Healthcare providers can include, for example, physicians, physician assistants, nurses, nurse practitioners, physical therapists, lab technicians and the like. The healthcare practice can also include one or more treatment rooms 36, test facilities 37 and surgical theaters 40. Treatment rooms can include, for example, locations in which a physician consults with her patient, were treatment is given to the patient. Test facilities 37 can include facilities such as x-ray facilities, MRI facilities, treadmills, ultrasound equipment, and laboratories, just to name a few.

As would be apparent to one of ordinary skill in the art after reading this description, various different healthcare practices may use other internal or external resources 44, 45 in the course of their practice. These and the other described resources can be communicatively coupled to one another, for example, using networking technology. Accordingly, electronic records and other data can be shared among the various resources to facilitate performance of a given resource's determined functions. Also, as noted above, the resources can include computing capabilities used in performance of their tasks.

As described in more detail below, client computing devices with clinical workflow management applications running thereon can be provided for use by personnel of the various resources to manage their tasks and responsibilities. These client computing devices can be handheld computing devices (e.g., tablet computers, iPads, smart phones, laptops, etc.) and can be communicatively linked to the healthcare provider network such that information (e.g. patient information, treatment information, prescription information, billing information, and so on) can be shared between the client devices and the various resources of the healthcare practice. In example embodiments discussed below, these client devices are described as handheld computing devices. However, after reading this description, one of ordinary skill in the art will understand how to implement the features and functionality described herein using desktop, wall-mounted, equipment-integrated, or other computing devices to perform the client computing functions.

A clinical workflow management service 48 can be included with the healthcare practice to manage the data and information in the healthcare practice and to provide information to the client computing devices. In various embodiments, clinical workflow management service 48 can be integrated with server 31 (e.g., an application running on server 31), it can be integrated with other computing resources in the healthcare facility, or it can be a stand-alone service with dedicated computing resources. Clinical workflow management service 48 can be configured to consolidate data and information from data storage facilities within healthcare facility (e.g., cloud storage 41, data storage 32, and data stored at various resources) as well as information received from sources external to the healthcare facility.

Clinical workflow management service 48 can be configured to gather this information and provide it to the one or more client computing devices used in the healthcare facility. For example, in some embodiments, clinical workflow management service 48 retrieves a predefined set of information (e.g. patient EHR, billing records, scheduling records, etc.) and provides this information to the client computing devices. The information can be tailored for one or more client computing devices or groups of client computing devices or all of the gathered information can be sent to the client computing devices. For example, particular pieces of information relevant to a resource with which a client computing device is associated can be culled from the full set of gathered information and sent to that associated client computing device. As a further example, patient health records and scheduling information may be gathered and sent to one or more client computing devices used by physicians or other healthcare providers 39 in the healthcare facility. Still further, in facilities where there are multiple healthcare workers (for example, physicians), patient records can be gathered and sorted such that each physician receives only that information pertaining to his or her patients.

As another example, billing and scheduling information might be gathered and sent to the billing department 34. Accordingly, client computing devices (or clinical workflow management applications running thereon) can be identified with specific personnel at the healthcare facility or with particular resources or functions of the healthcare facility. In this manner, tailored sets of information can be delivered to specific client computing devices to avoid the need to download all data to all devices. In some embodiments, the client computing devices are identified by information coded into the applications. In other embodiments, the client computing devices can be identified based on login information provided by healthcare worker. In this latter example, client computing devices can be shared amongst different practitioners, such, as for example, across different shifts.

Figure 2:
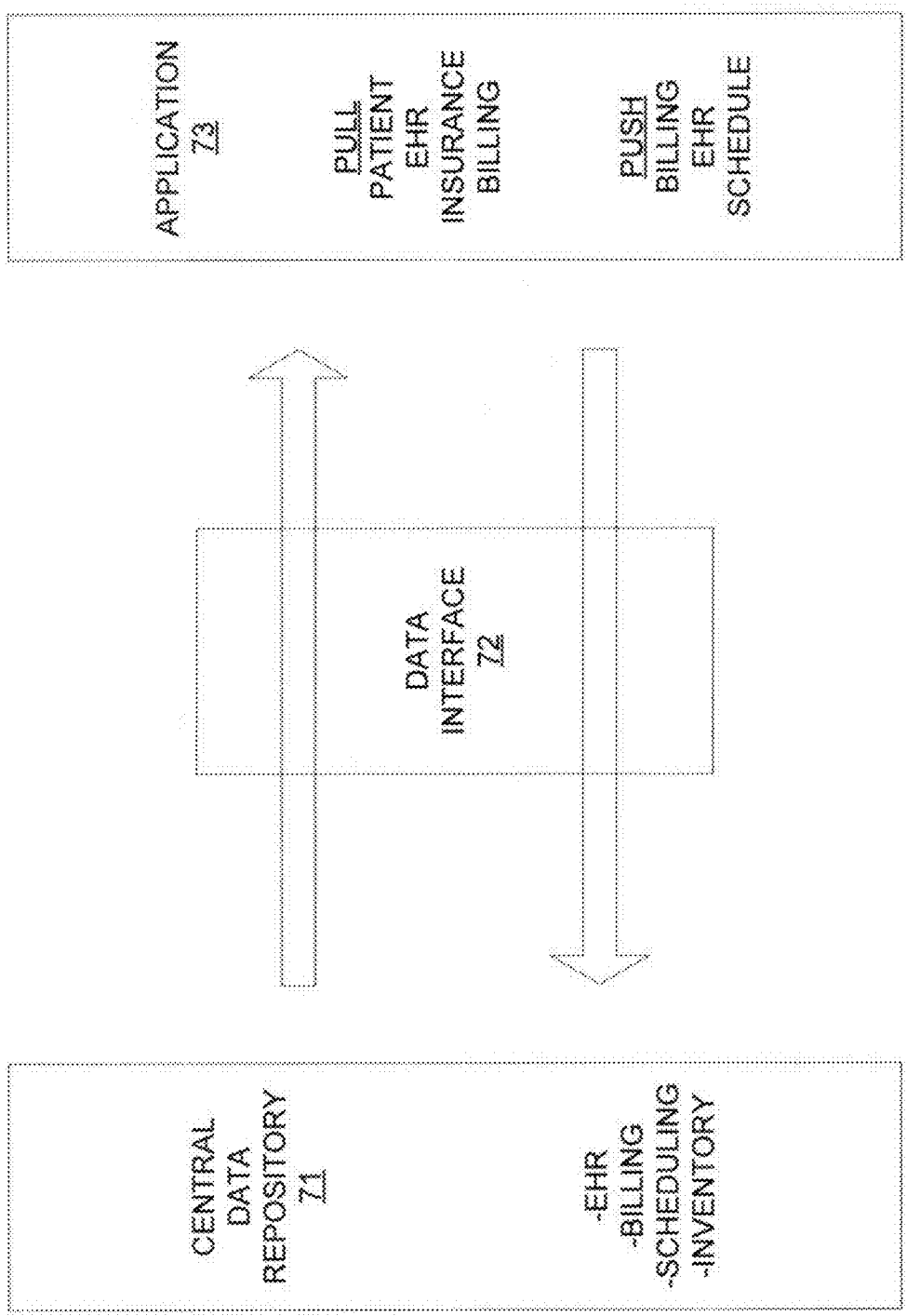
FIG. 2 is a high-level block diagram illustrating one example of information sharing in accordance with one embodiment of the technology described herein.

As stated above, in the example healthcare practice, the various resources can each include computing capabilities and various client computing devices can be provided for use as well. In order for these devices to operate well and for the functions of the healthcare practice to be integrated, these devices can be configured to share information with one another as may be relevant to their respective resource functions. FIG. 2 is a high-level block diagram illustrating one example of information sharing in accordance with one embodiment of the technology described herein. Referring now to FIG. 2, this example includes a central data repository 71, data interface 72, and one or more clinical workflow management applications 73.

Central data repository 71 can be configured to store records and information germane to the healthcare practice. For example, central data repository 71 can be configured to store EHR, patient billing records and other billing information, patient scheduling information, resource scheduling information, inventory information, and other information relevant to the healthcare practice. Central data repository can be a centralized data store or it can encompass data storage facilities distributed within and external to the healthcare practice. For example, central data repository 71 can encompass cloud storage 41, server data storage 32, and other data storage elements. By way of example, consider a hospital environment in which a plurality of different healthcare practices may be registered to admit and treat patients in the hospital. In such an environment, central data repository 71 can comprise data storage for the hospital data records, and clinical workflow management applications 73 from a plurality of different registered healthcare practices can be given access to the information in central data repository 71.

Clinical workflow management application 73 can include healthcare practice management applications running on one or more client devices used in the healthcare practice. Clinical workflow management application 73 can include the functionality to retrieve or pull information from data repository 71 including, for example, patient health records (e.g., EHR), scheduling information and billing information. Clinical workflow management application 73 can be a single application or it can include multiple applications running on a device. As described in further detail below, clinical workflow management application 73 can be configured to perform functions such as build a schedule for the healthcare practitioner assigned to or logged into a particular client computing device; provide patient health records and other patient information to the healthcare practitioner treating a patient; receive diagnosis and treatment information for a patient entered by a healthcare practitioner; receive prescription information for a patient from an attending physician or other healthcare practitioner; receive confirmation of delivery of prescribed materials; update inventory records based on materials prescribed and supplies used in treating a patient; update patient billing records based on information such as treatment provided, facilities and supplies utilized, materials prescribed, and the like; and receive scheduling information for future patient treatments or follow-ups.

In some embodiments, clinical workflow management application 73 can be one or more applications configured to run on their respective client computing devices. For example, different client devices for different facility resources may run different applications 73. For example, a physician's application 73 may be provided for use by a physician on his or her client computing device. Likewise, clinical workflow management application 73 tailored to a physician assistant, a nurse or nurse practitioner, a laboratory or test clinician, and other facility resources can be provided. In another embodiment, clinical workflow management application 73 can be a common application used by client computing devices at all of, or a subset of facility resources. Therefore, although the examples described herein in some instances refer to a specific clinical workflow management application 73 (e.g., a physician's application or a nurse's application) one of ordinary skill in the art after reading this description will understand that a common application can be provided to perform functions of the specific applications. In still other embodiments, the functions of clinical workflow management application 73 can be shared among a given client computing device and another computing resource such as, for example, workflow management 48.

Data interface 72 can be included to provide a communications interface between central data repository 71 and the one or more clinical workflow management applications 73 used in the healthcare practice. For example, data interface 72 can be provided to retrieve the necessary particular information from central data repository 71, and provide it to one or more designated clinical workflow management application 73. In some embodiments, data interface 72 can be configured to pull the information from central data repository 71 and broadcast it to all client devices or clinical workflow management application 73, or it can selectively send certain pieces of information or certain information types to specific client devices or groups of client devices. For example, data interface 72 can be configured to send billing records and billing information to all clinical workflow management application 73 or client devices, or only to those clinical workflow management applications 73 or client devices used by the billing department or that may be otherwise used by personnel who would benefit by having that information.

With Health Insurance Portability and Accountability Act (HIPAA) in particular and other privacy concerns in general, information storage in the various data storage locations associated with and external to the healthcare practice may be encrypted or otherwise protected. Additionally, because there can be a variety of different data types accessed by the system and the data can be stored at different data storage locations, the data retrieved by data interface 72 may be in different formats. Accordingly, in some embodiments, data interface 72 can be provided with functionality to decrypt data that has been encrypted with a variety of different encryption types and encryption keys, and to re-secure the data (e.g. re-encrypt the data) prior to delivering it to clinical workflow management application 73. Additionally, data interface 72 can be provided with functionality to access and read data in a variety of different data formats and data types, and translate that format into one that is legible to the clinical workflow management application 73.

In addition to retrieving data and providing to clinical workflow management application 73, data interface 72 can also be configured to receive data from clinical workflow management application 73 and push or send that data to central data repository 71. This data push can be used to update healthcare records and other information at central data repository 71 with information entered by healthcare practitioners or otherwise received from the healthcare facility in conjunction with the treatment or follow-up of the patients. For example, billing record updates, EHR updates, scheduling updates, prescription record updates, inventory updates, and other like information can be pushed by the clinical workflow management applications 73 to data interface 72 (or pulled by data interface 72 from the clinical workflow management applications 73) and provided to central data repository 71.

As with retrieval of data from central repository 71, data interface 72 can likewise ensure that the data is secure for transmission from application 73 to central repository 71, as well as perform any format changes necessary to provide the data in the proper format expected by the various components of central repository 71. For example, data sent encrypted using one encryption format by a clinical workflow management application 73 can be decrypted by data interface 72 and re-encrypted into an encryption format anticipated by central data repository 71. Because central data depository 71 can include data stored by a number of different systems, data interface 72 can be configured to decrypt information received from one source, and re-encrypt the information for transmission to various components or systems using their respective encryption techniques.

In addition to providing connectivity amongst the different aspects of a clinic or healthcare practice to allow for efficient data storage, retrieval, and/or processing, various embodiments are further directed to optimizing patient care so as to achieve the ideal (or as close to ideal as possible) recovery/care path for a patient. That is, information relevant to the recovery path for one or more patients can be obtained, aggregated, and/or analyzed to measure the success of a particular prescription (which can be a medication or device, such as a knee or elbow brace, etc.) or treatment protocol. Such information may include, but is not limited to the following: data associated with a patient's progress with physical or other rehabilitative therapy; how many times the patient has had to visit a doctor/clinic; what prescription has been assigned or implemented; periodic pain assessment data; and a patient's satisfaction with the treatment outcome. This information can be gleaned from the aforementioned patient EHR, billing records, scheduling records, etc., as well as from, e.g., an automated physical therapy system, which will be described below.

The automated physical therapy system may include a physical therapy application running on a client device, which may have the same or similar connectivity capabilities/functions of clinical workflow management application 73, and used by a patient for instructing the patient regarding the appropriate exercises to be performed for a particular physical therapy program, and to alert or remind the patient to perform the designated activities. In further embodiments, a detection apparatus such as an accelerometer or motion detector can be worn by the patient (or in some instances, such accelerometers, motion detectors, or other sensor devices may be incorporated into, e.g., a knee or elbow brace) and used to sense the motion of the patient to help track performance of the prescribed activities or exercises in real time. The motion sensing apparatus can be configured to communicate data regarding the sensed activity to the device running the application. The physical therapy application can use this information to track performance of the activity by the patient as well as to track the quality of the exercises performed by the patient. In other words, the motion sensor worn by the patient can measure movement of the patient or of a patient limb, sense the range of motion achieved during the activity or during each rep of the activity, provide information for each rep performed, and so on.

The physical therapy application can use the information received from the motion sensor to keep track of whether the patient has performed the appropriate exercises at the appropriate intervals, performed the prescribed number of reps, achieved a desired range of motion during exercise, and otherwise performed according to the prescribed regimen. The physical therapy application can cause this information to be stored on the client device and to be communicated to the caregiver or healthcare practitioner such that the patient's progress can be tracked regularly and, where desired, between office visits. Accordingly, the system can be configured to monitor the activity of the patient, measure the patient's performance during prescribed activities, record this information for record-keeping purposes, make this information available to the patient so he or she can track his or her own progress, and can communicate this information to a healthcare professional. The data can be presented to the patient and his or her health care provider in graphic, tabular, or other useful forms. The physical therapy application can also be configured as a two-way communication tool. For example, the physical therapy application in some embodiments can send information to the patient from the healthcare provider to send clinical notes, advice, or updates. The physical therapy application can also be configured to allow patients to monitor their own progress through graphs, charts, and data gather, logged and analyzed through the physical therapy application.

The following operational scenario illustrates and generally describes aspects of the technology set forth in this document. Typically, the process begins when the patient arrives at a physician's office (or the office of another healthcare professional) to receive treatment for injury. Upon arrival at the health care facility, the patient is greeted by an office coordinator in the physician's waiting room and is provided with an iPad, tablet or other computing device into which he or she may enter demographic data, data about his or her current and previous conditions and other relevant data. Additionally, electronic medical records brought to the office by the patient can be loaded into the iPad, tablet or other computing device to allow the patient medical records to be uploaded into the healthcare facility's databases.

Once the patient has completed the registration process, the patient meets with the healthcare practitioner to assess the condition and determine a procedure to treat the condition. Upon determining a procedure appropriate for the patient's condition, the physician coordinates the procedure. For example, surgery can be performed and the patient provided with a post-operative brace to be worn during the healing process. The physician can also provide direction to another healthcare practitioner, such as a trainer or physical therapist, to deliver a physical therapy solution for the patient.

The physical therapist (or other healthcare professional) logs into the healthcare practice's computing system to determine the workout routine for the patient's recovery. Accordingly, the automated physical therapy system may also include another physical therapy application (or another instance of the physical therapy application) running on a client device, which again may have the same connectivity capabilities/functionality as clinical workflow management application 73. However, this physical therapy application (physician-side physical therapy application as opposed to the patient-side physical therapy application) may be utilized by the clinic or healthcare facility/physician(s) to manage and control the physical therapy for the patient, access information from, e.g., central data repository 71, etc. The healthcare practice may already have predefined protocols for various injuries and the healthcare practitioner may prescribe these predefined protocols for the patient. Alternatively, custom protocols can be defined for a given patient, entered into the healthcare practice's computing system at the clinic and made accessible to the practitioner. The healthcare practitioner identifies the protocols appropriate for the patient and any additional exercises that may be recommended. Because the patient information has already been entered into the healthcare practice database, e.g., central data repository 71, the healthcare practitioner can easily identify the patient from a list of available patients and review any patient information necessary when identifying the physical therapy routines.

In some embodiments, the system generates a code that can be provided to the patient to use for downloading the physical therapy application. Preferably, the code is patient specific such that patient information and prescribed routines can be identified on a patient-by-patient basis, and patient unique information can be provided to the patient when he or she logs into the system. The code can be automatically e-mailed or text messaged to the patient based on patient information in the system. Alternatively, for privacy purposes the code can be provided to the patient directly at the time of the visit. An e-mail or other electronic message can also be sent to the patient with a link to download the application that the patient will use for the automated physical therapy routines.

When the patient logs onto the system and downloads the physical therapy application, the patient code, or ID, identifies the patient to the healthcare facility computing system. In response, the healthcare practice's computing system identifies the protocols (pre-built or custom) prescribed for the patient and provides those to the patient along with the physical therapy application. Accordingly, delivery of the physical therapy application includes delivery of protocols prescribed for the patient. Accordingly, the physical therapy application can be configured to connect to the appropriate data storage (e.g. cloud storage) retrieve the appropriate physiotherapy routines for the patient as well as accompanying instructional videos and other information. The patient can then initiate the physical therapy application and perform the physical therapy exercises under the guidance of the physical therapy application.

The patient-side physical therapy application can be configured to guide the patient through each step of the exercise. In some embodiments, the patient-side physical therapy application can further be configured to present the exercises in a game-like fashion, which can help to keep the patient engaged with the exercise. Alerts can be provided to the healthcare practitioner informing the practitioner of the patient's progress or letting the practitioner know where the patient has failed to perform the prescribed exercises. When the patient achieves the prescribed protocols, the patient can receive an indication of success, which is also shared with the healthcare practitioner.

The healthcare practice/physician-side physical therapy application can be used to monitor a large number of physical therapy episodes and monitor progress with an integrated view of all active patients. Because progress can be reported electronically and the data displayed graphically, it is easier for the healthcare practitioner to get a snapshot of his or her patient's progress. Additionally, surveys can be provided to the patient to obtain information about how the patient is feeling, about their strength, mobility, etc. This information is collected and can also be provided to the healthcare practitioner to facilitate assessment of the patient's progress and condition. Compliance and progress can be monitored for each patient as well as plotted data results of mobility versus survey-specific data demonstrating how the patient is feeling during recovery. This data can be combined in selected as desired to provide a graphic representation of the patient's recovery. The information can also be used in conjunction with insurance payors/billers to send supporting data with insurance claims to support the ACO (accountable care organization) and other billing models with outcomes data for the patient.

As described above, a healthcare provider or clinic entity may wish to assess the business-related performance of the clinic by obtaining and analyzing clinical data to promote efficient management of the healthcare practice, reduce costs, identify areas for improvement, and receive suggestions to realize such improvements. Accordingly, a request for clinical data filtering can be made via a business intelligence application, which again may have the same or similar connectivity/functionality of clinical management workflow application 73 and the physical therapy application.

Figure 3:
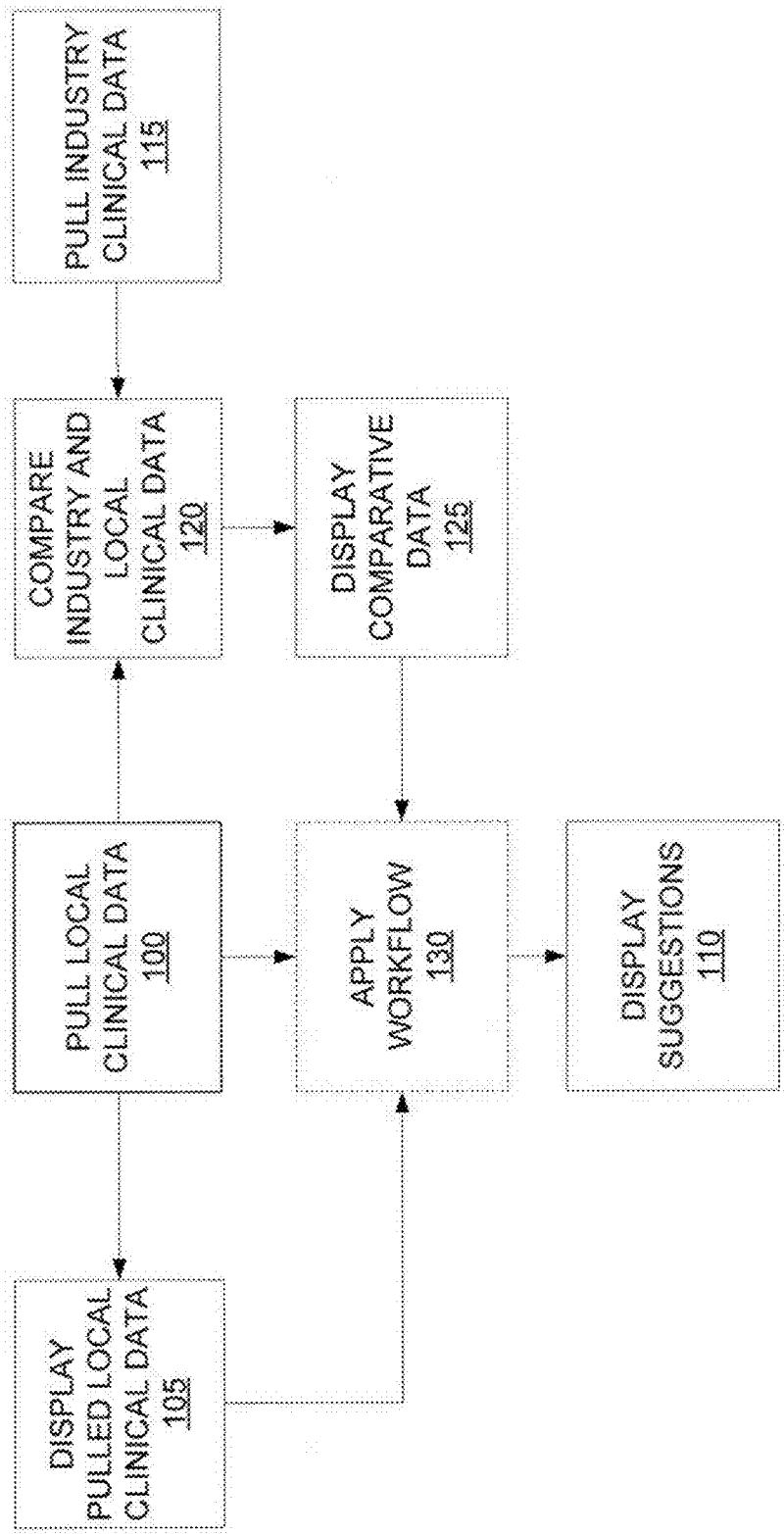
FIG. 3 is a high-level operational diagram illustrating various processes that can be performed for achieving business workflow management in accordance with one embodiment of the technology described herein.

FIG. 3 is a high-level operational diagram illustrating various processes that can be performed for achieving business workflow management in accordance with one embodiment. At operation 100, local clinical data is pulled. As utilized in this context, the term "local" can refer to clinical data that is associated with a clinic or healthcare practice as previously described, and not necessarily only where such clinical data may be stored or obtained from, which can be distinguished from "industry" clinical data, as will be described in greater detail below. In pulling such local clinical data, one or more filters, e.g., a set of filters, may be applied such that the appropriate local clinical data is retrieved based on the request. For example, if local clinical data associated with a particular patient, a particular prescription, certain billing information, etc. is requested, the one or more filters can be utilized to selectively obtain that local clinical data.

At operation 105, the pulled local clinical data can simply be displayed on a client device via the business intelligence application. Accordingly, the requestor, e.g., a healthcare practitioner, a business administer of the clinic, etc. may see or otherwise be presented with the local clinical data in a raw form. Alternatively, in addition to displaying the local clinical data, at operation 110, suggestions applicable to the pulled local data may be displayed. For example, suggestions can include, but are not limited to, whether or not a particular medication or device (e.g., a knee or elbow brace), should still be prescribed to patients, whether or not a particular protocol should be utilized for a particular patient/ group of patients, whether or not the inventory associated with a particular device should be replenished, etc. Still another example can entail evaluating data associated with each location of a clinic, where the characteristics of each location can include, e.g., inventory or product mix, and product run for each location, pricing, and so on. Accordingly, the business intelligence application may suggest ways to alter these characteristics to improve business performance (e.g., financial performance, efficiency, etc.) or patient outcome performance (e.g., better success rates with less patient visits to the clinic). Appropriate suggestions may include, for example, revising the inventory to stock more high-use products, more high-margin products, or more products that have longer shelf lives.

That is, suggestions can be, for example, procedures, measures, or other business actions that the clinic can take to improve business workflow. Alternatively still, such suggestions may be directly displayed to a user, bypassing the display of the pulled local clinical data at operation 105.

Additionally, at operation 115, industry clinical data can be pulled. That is, the aforementioned set of filters, for example, can be applied to clinical data that has been accumulated on an industry-wide basis, whether nationally, regionally, internationally, etc. Pulling such industry clinical data can be relevant when attempting to determine industry trends, practices, revenues, etc. as a point of comparison, or as a type of performance benchmark. Accordingly, at operation 120, the pulled local clinical data and the pulled industry clinical data may be compared, and at operation 125, the comparative data can be displayed. Further still, suggestions can be displayed based on the comparative data. Like the suggestions applicable to the pulled local data, suggestions can also be made based on, e.g., how the local clinical data matches or fails to match up with the industry clinical data. For example, if a particular protocol for rehabilitating patients with a particular medical issue appear to result in a better success rate than the protocol being utilized by the clinic, a suggestion can be made to implement the industry-used protocol at the clinic.

Optionally, at operation 130, a workflow may be applied prior to displaying the aforementioned suggestions. By applying a workflow, the suggested procedures or measures that can be taken may be presented as, e.g., progressive steps that the clinic can undertake. In a scenario where multiple suggestions are made by the business intelligence application, the multiple suggestions (and/or their respective aspects) can also be ordered in a certain workflow.

It should be noted that the display or presentation of clinical data and/or suggestions can be in any appropriate format, e.g., through the use of visual graphs, through the display of numerical/textual data, a spreadsheet format that can be displayed on a client device, or otherwise exported to another computing system, etc. Additionally, such displays of data can be interactive, such that a user may adjust the pulled data by, e.g., adjusting certain variable factors (which can also be specified in the set of filters for pulling clinical data), applying a suggested action to existing pulled data to see the effects of implementing the suggested action, etc. For example, a business administrator of the clinic, may be presented with a graphical representation of a clinic's profits as a function of particular prescribed braces. By interacting with the graphical representation, the business administrator may adjust data regarding usage of the prescribed braces (based on a suggestion) to see how profits can be affected. As another example, the business administrator may be presented with "overall" clinical data that may be aggregated from each facility operated by the clinic, and the business administrator may interactively select a particular facility to obtain more detailed clinical data specific to that particular facility.

Figure 4A:
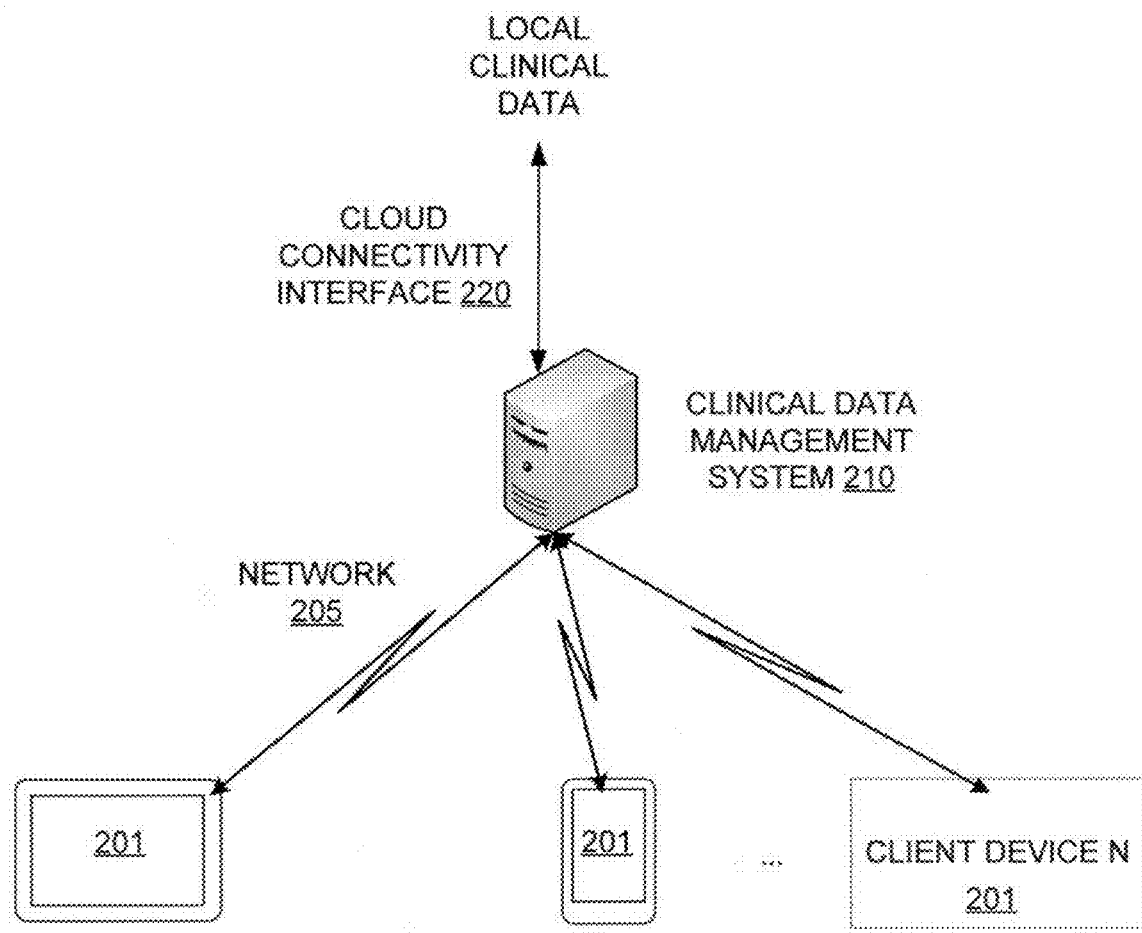
FIGS. 4A and 4B illustrate an example business intelligence portal or system for implementing business intelligence technology in accordance with one embodiment of the technology described herein.
Figure 4B:
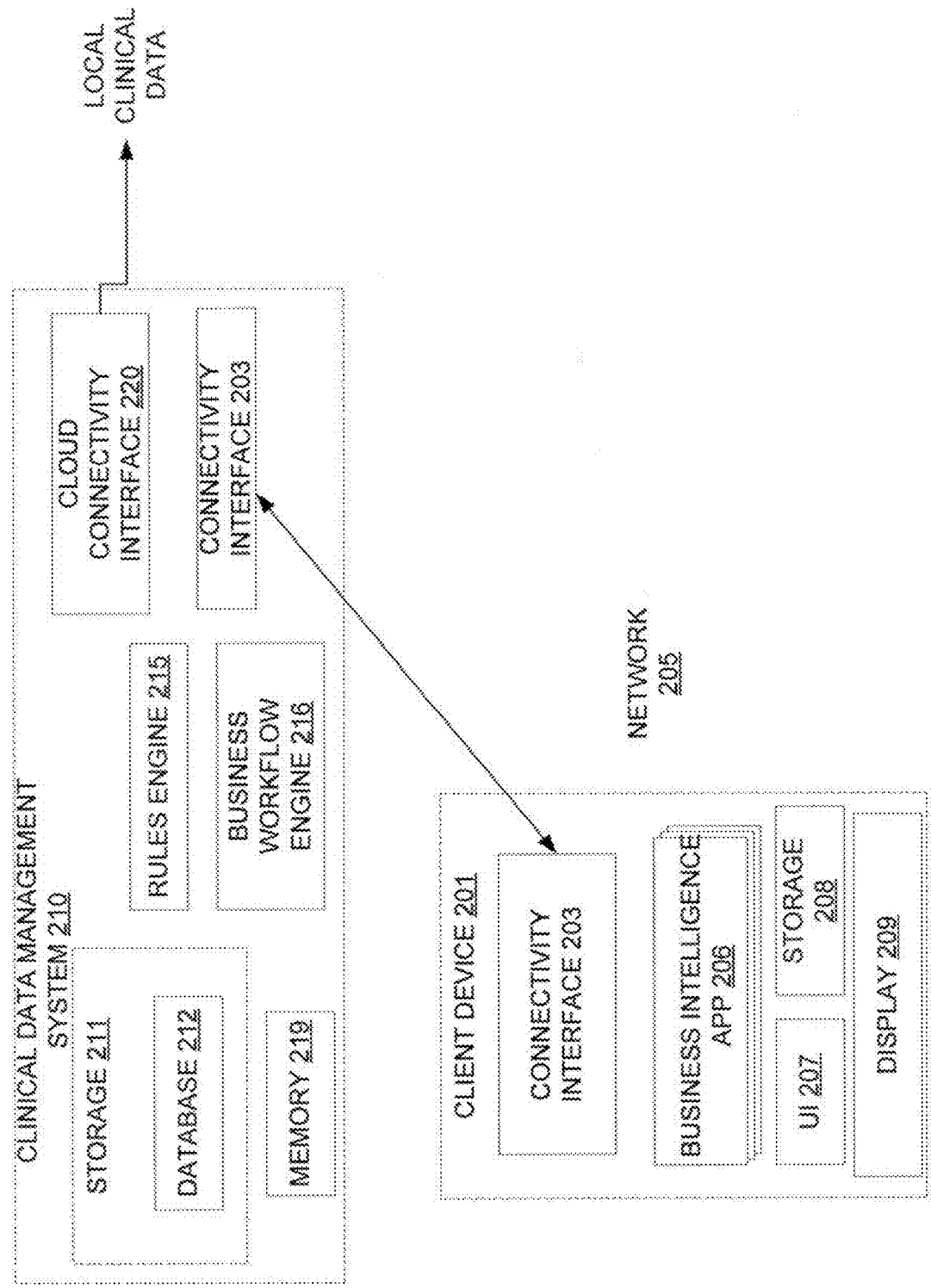

FIGS. 4A and 4B illustrate an example business intelligence portal or system for implementing business intelligence technology in accordance with one embodiment of the present disclosure. A plurality of client devices 201 may communicate with clinical data management system 210 over network 205 for the remote analysis of clinical data (for example, orthopedic data, local, industry, or regional-based) for business performance, trending, and suggestive action based at least in part, on clinical data provided by a clinic.

Client devices 201 may comprise any hand-held computing device (tablets, PDA's, smartphones, cellphones, palmtops, etc.); workstations or servers; or any other type of general-purpose computing device configured to run business intelligence application 206 and output it on a display 209.

Communications network 205 may include, e.g., a cellular telephone network, an ad hoc network, an intranet, an extranet, a virtual private network (VPN), a local area network (LAN), a wireless LAN (WLAN), a wide area network (WAN), a portion of the Internet, a portion of the Public Switched Telephone Network (PSTN), or any combination thereof. The communications network may use a number of communication mediums. The communication medium may be, for example, a wireless network system such as a cellular network, a wireless personal area network, a wireless local area network, or other similar communication medium. The communication medium may alternatively be a wired system, such as a coaxial cable system, a fiber optic cable system, an Ethernet cable system, or other similar communication medium.

The output of business intelligence application 206 may compare local clinical data with industry clinical data stored on database 212. As described previously, such a comparison may provide a business performance evaluation, trending, and suggestive action for the clinic. For example, a suggestive action may inform a clinic that they are pricing medical products too high relative to other clinics in the same region and industry. This business performance evaluation, trending, or suggestive action may be output on the display 209 of client device 202 via user interface 207 for business intelligence application 206.

Accordingly, and referring back to FIGS. 2 and 3, the business intelligence portal or system may operate as follows. At operation 100, client device 201 may initiate a request at business intelligence application 206 to pull local clinical data from clinical data management system 210. The local clinical data may be stored, for example, in central data repository 71, and can include, e.g., one or more patients' EHR, billing records, scheduling information, inventory information (e.g., product, medication, etc.)

Clinical data management system 210 may be a server or distributed server system having a storage 211 that includes a database 212 configured to store local clinical data gathered from a variety of clinical clients operating a variety of clinical systems, for example, a billing system, a scheduling system, and an EHR clinical system. Clinical systems may include servers configured to store patient information for clients. Financial data stored at billing system may include, for example, data relating to billing records for each product, profits, revenues and margins, accounts receivable, product warranty costs, carrying costs, and shipping charges. Scheduling data stored at scheduling system may include, for example, data relating to patient name, physician, appointment time, appointment data, a physician's appointment calendar, and the clinic's appointment calendar. EHR may include data relating to patient treatment such as medical history, medication and allergies, laboratory test results, immunization status, vital signs, radiology images, demographics, age, weight, gender, residence, and income.

Clinical data management system 210 may include a cloud connectivity interface 220 for pulling local clinical data over a network from a variety of sources (whether internal or external to a healthcare practice as described above). Connectivity interface 220 may have the flexibility to effectuate connections via HL7, Web Services, XML, S-FTP, secure drop box, and other standards generally related to the exchange, retrieval and sharing of electronic health information. Hence, clinical data management system 210 may be implemented as a part of or within the healthcare practice illustrated in FIG. 1, e.g., as part of or within server 31. Alternatively, the business intelligence portal or system may be implemented as its own, e.g., standalone system, that may operate within or in conjunction with the healthcare practice of FIG. 1.

Again, local clinical data can be pulled at operation 100 using a set of filters that may specify or correspond to a business rule that in turn, can be specified by rules engine 215. At operation 115, industry clinical data may be pulled from storage 211 also using the set of filters/business rule specified in rules engine 215. Rules engine 215 may also be configured to compare the local clinical data to the industry clinical data at operation 120, as well as provide one or more business suggestions to a user of client device 201 (e.g., a healthcare practitioner, business administrator, etc.) The business suggestion(s) may be specified as a workflow at operation 130 determined by workflow engine 216. In alternative implementations, rules engine 215 may be applied to industry clinical data temporarily stored in memory 225 disposed in clinical data management system 210. Ultimately, the resultant local and/or industry clinical data, as well as any suggestive actions (whether or not as a workflow) at operations 105, 110, and 125, may be presented on display 209 of client device 201 via user interface 207 of business intelligence application 206.

In alternative implementations, workflow engine 216 and rules engine 215 may be implemented using a processor (not pictured) disposed on client device 201. In such alternative implementations, client device 201 may initiate a request at business intelligence application 206 for clinical data management system 210 to transmit unfiltered clinical data (e.g. national clinical data on product inventory) pulled using cloud connectivity interface 220. The clinical data may then be transmitted to client device 201 over network 205. Client device 201 may temporarily or permanently store the data in storage 208. After filtering and/or performing the requisite comparisons and/or analysis to provide suggestions, the clinical data and/or suggestions may be displayed on display 209 of client device 201 via user interface 207 of business intelligence application 206.

Figure 5:
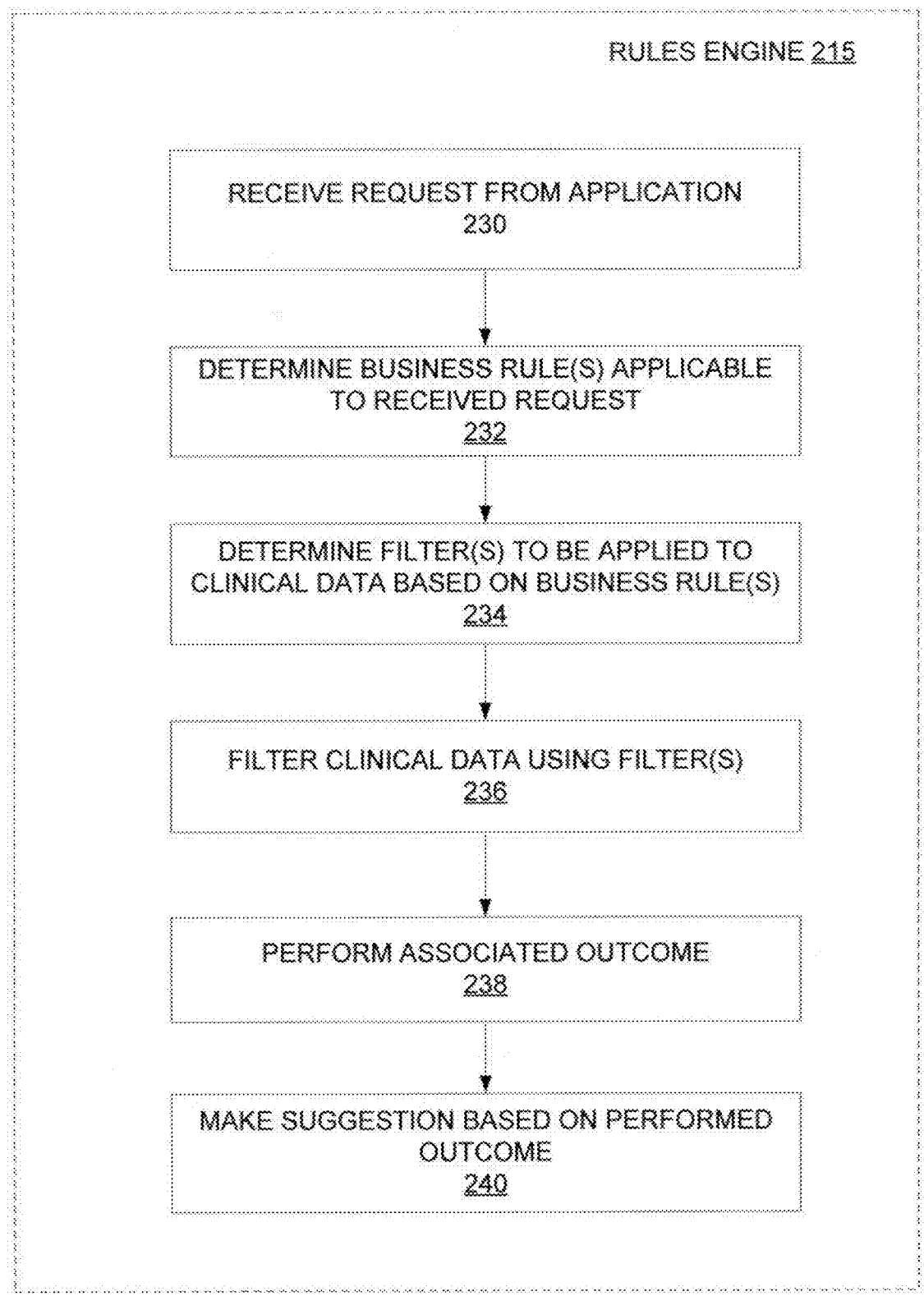
FIG. 5 is an operational flow diagram illustrating an example process performed by a rules engine for filtering clinical data and ultimately determining suggestive actions to implement in accordance with one embodiment of the technology described herein.

Referring now to FIG. 5, an operational flow diagram illustrates an example process performed by rules engine 215 for filtering clinical data and ultimately determining suggestive actions to implement via business intelligence application 206. At operation 230, rules engine 215 may receive a request from business intelligence application 206 regarding at least one business workflow management-related aspect of a clinic. The request may be for the ultimate display of local clinical data relevant to one or more aspects of business workflow management of a clinic, the display of industry clinical data, e.g., as compared to the local clinical data, or suggestive actions that the clinic may undertake.

At operation 232, one or more business rules applicable to the received request can be determined. Referring to FIG. 6, examples of business rules are illustrated. It should be appreciated that the business rules illustrated and described herein are meant to be illustrative examples only, and not limiting in any way. These business rules may represented as an action 300 and outcome 310 combination. For example, action 301 may involve pulling billed dollars and received AR (accounts receivable) from billing and ERP (enterprise resource planning) systems. The resulting outcome 311 may involve unifying dispensation data in order to visualize billed dollars. Another example, action 305 may involve reviewing order cycles and shipping charges, while outcome 315 may include providing intelligence on how to bulk order and/or modify par levels. That is, an action 300 can indicate the requisite filter or set of filters utilized by rules engine 215 to pull the appropriate local and/or industry clinical data for display and/or analysis. Hence, at operation 234, the filter(s) to be applied to the clinical data can be determined based on the business rule(s) to utilize in filtering clinical data to obtain a data subset of the clinical data applicable to the at least one business workflow management-related aspect.

At operation 236, the clinical data can be filtered using the determined filter(s) to obtain the data subset of the clinical data. At operation 238, the corresponding outcome can be performed to analyze the data subset of the clinical data in the context of business workflow management. That is, an outcome 310 can indicate the requisite analysis to be performed (and rules engine 215 can perform such analysis using, e.g., one or more algorithms, lookup tables, comparative computing methods, etc.) on the pulled clinical data, as well as an actual suggestive action. Hence, at operation 240, a suggestion can be made based on the performed outcome for improving business workflow management of the clinic based on results of the performance of the corresponding outcome process. Depending on the particular business rule, one or more algorithms can be applied to the result(s) of an outcome to generate one or more suggestive actions that can be presented, as will be discussed in greater detail below. For example, action 303 can involve pulling clinical data related to scheduling and EMR, while outcome 313 can involve evaluating, e.g., current efficiency and processes in place at the clinic. In this example, rules engine 215 may further apply one or more algorithms to generate suggestive action (s) based on the resulting evaluation determined by performing outcome 313.

Another illustrated example business rule includes action 304 and outcome 314, where Emergency Medical Room (EMR) data can be monitored/checks to look at patient care and recovery cycles. The EMR data would show when a patient was admitted and possibly readmitted. Outcome 314 includes evaluating the outcomes and effectiveness of a product use against each code, e.g., International Statistical Classification of Diseases (ICD) codes such as ICD-9/ICD-10, which are codes assigned to every diagnosis, description of symptoms, and cause of death attributed to human patients. That is, the outcome for patients can be evaluated along with any products/medication used for those patients. If that series of patients was readmitted because of a particular faulty product such a brace, the business rule may identify this issue, and may further provide a suggestion for using a different product.

As indicated, one or more algorithms may be applied to pulled clinical data (whether local or industry/regional clinical data) or to data resulting from the performance of an outcome at rules engine 215. Some broad examples of algorithms that can be utilized are as follows: classification algorithms for predicting one or more discrete variables based on other attributes in a data set; regression algorithms for predicting one or more continuous variables, such as profit or loss; segmentation algorithms which can be utilized to divide data into groups or clusters of data sets that may have similar characteristics; association algorithms that can be relied upon to identify one or more correlations between various attributes in a data set; and sequence analysis algorithms which can summarize frequency sequences or episodes discovered in data. Still other mechanisms may be utilized in accordance with various embodiments for processing and analyzing data, as well as generating suggestive actions, such as decision trees, artificial intelligence techniques, neural network algorithms, etc.

Actual suggestions may also be obtained or determined through the use of lookup tables or relationship databases. For example, pulled clinical data may relate to product mix and success rate of products in that product mix at a particular clinic location. Upon associating products in the product mix based on the success rates, and based on one or more performance thresholds, a lookup table can be accessed and an appropriate suggestive action can be obtained to be presented to a user of business intelligence application 206.

It should be noted that the business rules and the algorithms can applied to statistical clinical data, where, for example, pain experienced by a patient during recovery, a patient's satisfaction or lack of satisfaction can be recorded or translated into a numerical score, which can then be analyzed and/or operated on by one or more business rules and algorithms. Depending on one or more parameters set by a user of the business intelligence portal, for example, through UI 207 of business intelligence application 206, or predefined in, e.g., rules engine 215, pulled clinical data can be weighted to have more or less relevance with respect to a particular request.

Certain variable factors can also be considered or ignored to fine-tune or tailor the display of clinical data and the presentation of suggestive actions. For example, a healthcare practitioner may be interested in determining a "best" rehabilitation protocol without regard to cost. As another example, a business administrator of a clinic may desire to see greater trends by specifying that rules engine 215 pull broader clinical data by utilizing fewer parameters over a greater number of patients.

Figure 7:
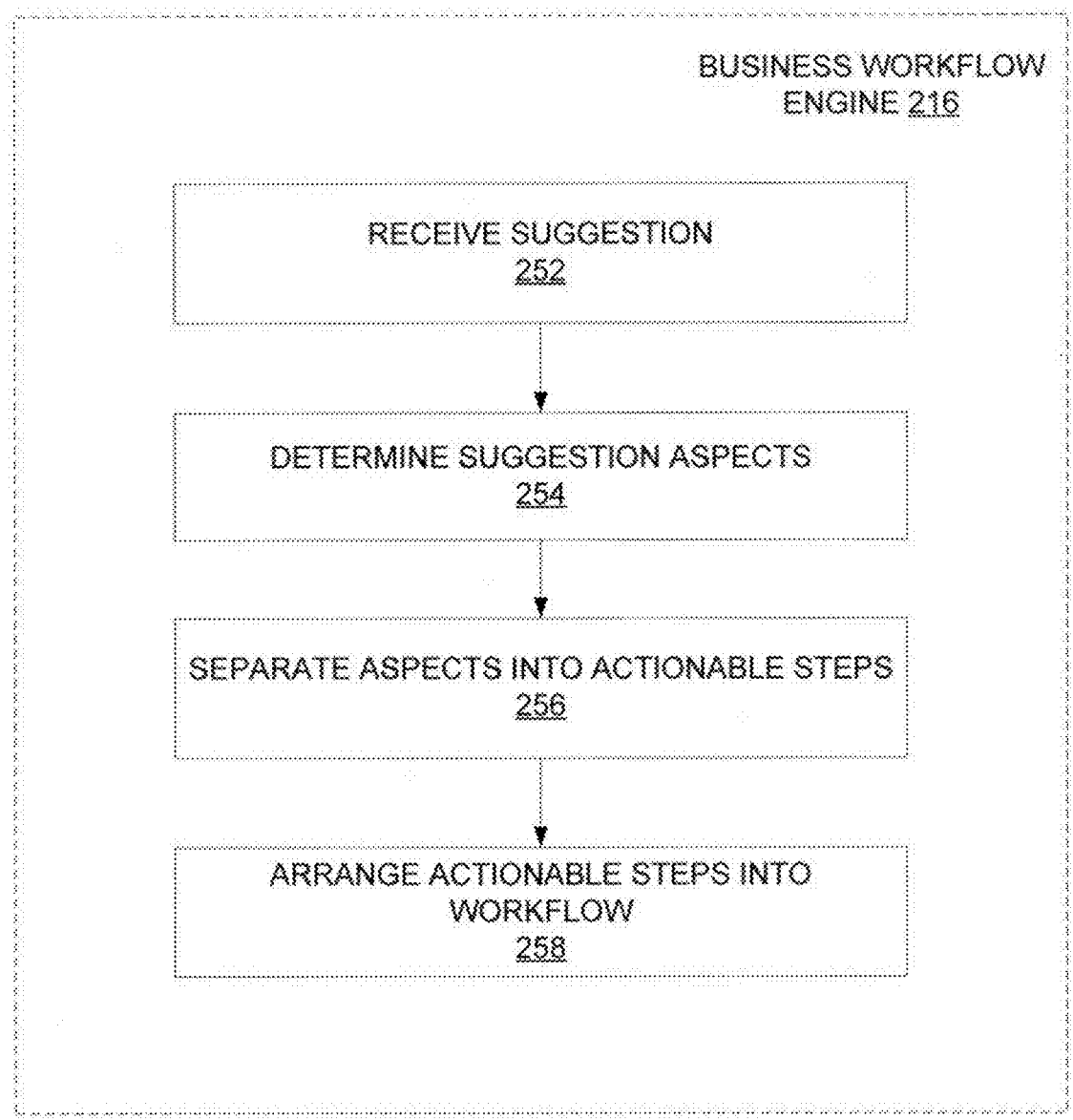
FIG. 7 is an operational flow diagram illustrating an example process performed by a workflow engine for applying a workflow to one or more suggestive actions in accordance with one embodiment of the technology described herein.

FIG. 7 is an operational flow diagram illustrating an example process performed by workflow engine 216 in accordance with one embodiment. As previously described one or more suggestions may be organized into a workflow for presentation to a user through application of workflow engine 216. At operation 252, workflow engine 216 receives a suggestion. The suggestion may be received from rules engine 215, and may be the result of processing a business rule and/or application of one or more algorithms to pulled clinical data.

At operation 254, one or more aspects of the suggestion may be determined. For example, workflow engine 215 may receive a suggestion regarding how to improve patient outcomes based on pulled physician notes from EMR and by linking data gleaned from the pulled physician notes to product use a physical therapy system. This can be the result of a business rule including action 306 and outcome 310 illustrated in FIG. 3. The suggestion to improve patient outcomes may involve utilizing a new product and implementing a new or revised protocol for rehabilitation. Accordingly, a first aspect of the suggestion may be utilization of the new product, such as a new knee or elbow brace. It follows that a second aspect of the suggestion may be the new or revised protocol for rehabilitation utilizing the new product.

At operation 256, the aspects may be separated into actionable steps, and the actionable steps may be arranged into a particular workflow at operation 258. That is, utilization of the new product can be separated into one or more actionable steps, such as purchasing the new product, updating inventory at one or more clinic locations with the new product, and implementing training for healthcare practitioners regarding the new product. The second aspect of the suggestion, the new or revised protocol for rehabilitation utilizing the new product can be separated into, e.g., the following actionable steps: translating the new or revised protocol into a distributable format that can be distributed to healthcare practitioners; providing training on the new or revised protocol; obtaining feedback from the healthcare practitioners and/or patients regarding the new or revised protocol; and assessing the effectiveness of the new or revised protocol after a predetermined amount of time to confirm the veracity of the suggestion, and whether or not the new or revised protocol should continue to be utilized.

At operation 258, the actionable steps may be arranged into a workflow that can be displayed on display 209 of client device 201. Presentation of the workflow can be through visual and/or textual means, through audio-video presentations, etc. that describe the actionable steps.

Figure 8:
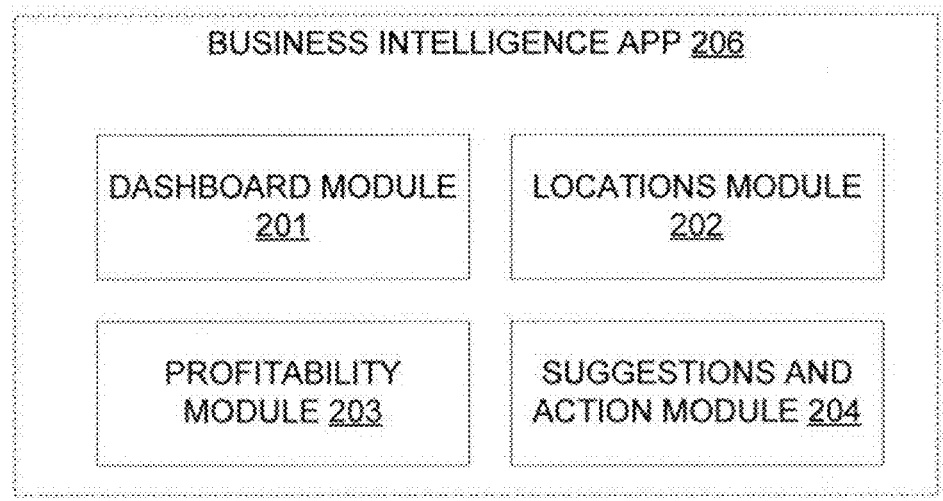
FIG. 8 illustrates example operational modules of a business intelligence application in accordance with one embodiment of the technology described herein.

With reference now to FIG. 8, the operation of business intelligence application 206 is illustrated. Business intelligence application 206 may comprise a dashboard module 201, a locations module 202, a profitability module 203, and a suggestions and action module 204. These modules may be implemented separately or as a combined module. Moreover, these modules may display clinical data on display 209, individually or in combination (e.g. two modules, three modules, or four modules) in any arrangement. These modules may display different clinical data in response to user input (for example, mouse input, keyboard input, touch gestures, or voice recognition) into UI 207.

Dashboard module 201 may be configured to display detailed analytical information of local and/or industry clinical data. For example, dashboard module 201 may show a visualization about the inventory moving through any clinic or system. For example, it could display upper extremity bracing, lower extremity bracing, revenue dollars, and other basic dollar metrics from in relation to a clinic. Dashboard 201 may display product flow and inventory levels through a number of charts such as pi charts, histograms, and bell curves.

Locations module 202 may be configured to graphically display each physical location in a client's clinic and allow for deeper analytics for each location. For example, if a user clicks on any location in the location display, for that particular location the daily metrics for the following may be output: earnings, number of patients, number of transactions, and specific patients that received treatment.

Profitability module 203 may be configured to provide general clinical accounting information. For example, it may show billed dollars for the clinic against the products dispensed. Suggestions and actions module 204 may display specifically formulated suggestions based on the data that the system is monitoring.

It should be noted that any clinical data pulled, processed, and analyzed can be pulled from any database, storage facility, or other like resource whether internal or external to the healthcare practice (as illustrated in FIG. 1), such as central data repository 71. Such clinical data can include any clinical or business workflow management-related data whether originated at or by a clinic or healthcare practice, e.g., via the aforementioned physician-side physical therapy application or the patient-side physical therapy application.

The technology disclosed herein may promote revenue acceleration and efficiency in business workflow management. For example, the business intelligence portal/system and application may determine if the pricing of a clinic's products are set too high relative to the industry standard and make recommendations based on that industry standard. In another example, the business intelligence portal/system and application may return a historical graph showing billing as a series of linear data points. Any discrepancies in billing could stand out and the user of the business intelligence portal/system and application could take appropriate action.

Figure 9:
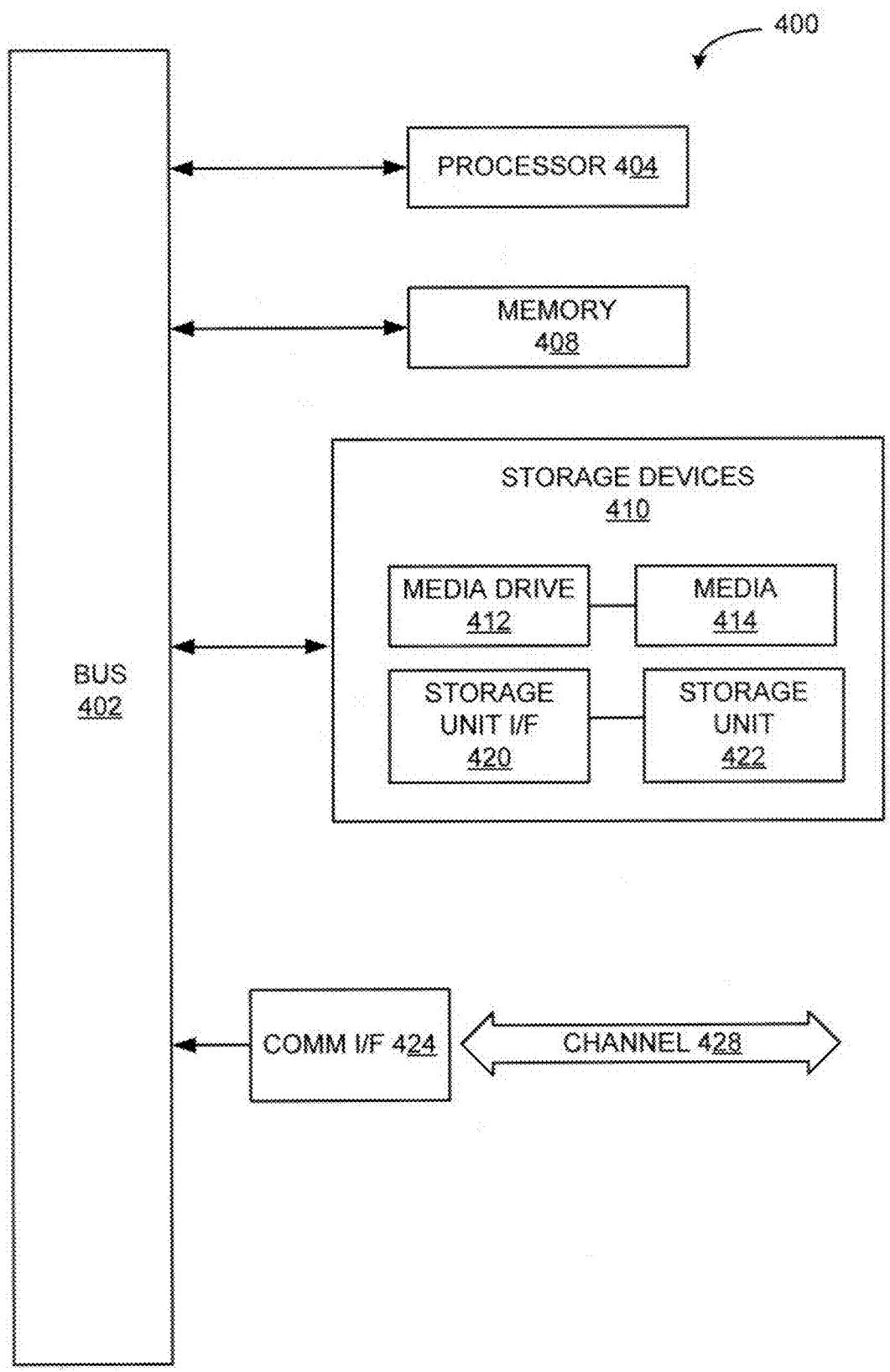
FIG. 9 is a diagram illustrating an example computing module that can be used to implement various features of the systems and methods described herein.

As used herein, the term module might describe a given unit of functionality that can be performed in accordance with one or more embodiments of the technology disclosed herein. As used herein, a module might be implemented utilizing any form of hardware, software, or a combination thereof. For example, one or more processors, controllers, ASICs, PLAs, PALs, CPLDs, FPGAs, logical components, software routines or other mechanisms might be implemented to make up a module. In implementation, the various modules described herein might be implemented as discrete modules or the functions and features described can be shared in part or in total among one or more modules. In other words, as would be apparent to one of ordinary skill in the art after reading this description, the various features and functionality described herein may be implemented in any given application and can be implemented in one or more separate or shared modules in various combinations and permutations. Even though various features or elements of functionality may be individually described or claimed as separate modules, one of ordinary skill in the art will understand that these features and functionality can be shared among one or more common software and hardware elements, and such description shall not require or imply that separate hardware or software components are used to implement such features or functionality.

Where components or modules of the technology are implemented in whole or in part using software, in one embodiment, these software elements can be implemented to operate with a computing or processing module capable of carrying out the functionality described with respect thereto. One such example computing module is shown in FIG. 9. Various embodiments are described in terms of this example-computing module 400. After reading this description, it will become apparent to a person skilled in the relevant art how to implement the technology using other computing modules or architectures.

Referring now to FIG. 9, computing module 400 may represent, for example, computing or processing capabilities found within desktop, laptop and notebook computers; hand-held computing devices (PDA's, smart phones, cell phones, palmtops, etc.); mainframes, supercomputers, workstations or servers; or any other type of special-purpose or general-purpose computing devices as may be desirable or appropriate for a given application or environment. Computing module 400 might also represent computing capabilities embedded within or otherwise available to a given device. For example, a computing module might be found in other electronic devices such as, for example, digital cameras, navigation systems, cellular telephones, portable computing devices, modems, routers, WAPs, terminals and other electronic devices that might include some form of processing capability.

Computing module 400 might include, for example, one or more processors, controllers, control modules, or other processing devices, such as a processor 404. Processor 404 might be implemented using a general-purpose or special-purpose processing engine such as, for example, a microprocessor, controller, or other control logic. In the illustrated example, processor 404 is connected to a bus 402, although any communication medium can be used to facilitate interaction with other components of computing module 400 or to communicate externally.

Computing module 400 might also include one or more memory modules, simply referred to herein as main memory 408. For example, preferably random access memory (RAM) or other dynamic memory, might be used for storing information and instructions to be executed by processor 404. Main memory 408 might also be used for storing temporary variables or other intermediate information during execution of instructions to be executed by processor 404. Computing module 400 might likewise include a read only memory ("ROM") or other static storage device coupled to bus 402 for storing static information and instructions for processor 404.

The computing module 400 might also include one or more various forms of information storage mechanism 410, which might include, for example, a media drive 412 and a storage unit interface 420. The media drive 412 might include a drive or other mechanism to support fixed or removable storage media 414. For example, a hard disk drive, a floppy disk drive, a magnetic tape drive, an optical disk drive, a CD or DVD drive (R or RW), or other removable or fixed media drive might be provided. Accordingly, storage media 414 might include, for example, a hard disk, a floppy disk, magnetic tape, cartridge, optical disk, a CD or DVD, or other fixed or removable medium that is read by, written to or accessed by media drive 412. As these examples illustrate, the storage media 414 can include a computer usable storage medium having stored therein computer software or data.

In alternative embodiments, information storage mechanism 410 might include other similar instrumentalities for allowing computer programs or other instructions or data to be loaded into computing module 400. Such instrumentalities might include, for example, a fixed or removable storage unit 422 and an interface 420. Examples of such storage units 422 and interfaces 420 can include a program cartridge and cartridge interface, a removable memory (for example, a flash memory or other removable memory module) and memory slot, a PCMCIA slot and card, and other fixed or removable storage units 422 and interfaces 420 that allow software and data to be transferred from the storage unit 422 to computing module 400.

Computing module 400 might also include a communications interface 424. Communications interface 424 might be used to allow software and data to be transferred between computing module 400 and external devices. Examples of communications interface 424 might include a modem or softmodem, a network interface (such as an Ethernet, network interface card, WiMedia, IEEE 802.XX or other interface), a communications port (such as for example, a USB port, IR port, RS232 port Bluetooth® interface, or other port), or other communications interface. Software and data transferred via communications interface 424 might typically be carried on signals, which can be electronic, electromagnetic (which includes optical) or other signals capable of being exchanged by a given communications interface 424. These signals might be provided to communications interface 424 via a channel 428. This channel 428 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to media such as, for example, memory 408, storage unit 420, media 414, and channel 428. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing module 400 to perform features or functions of the disclosed technology as discussed herein.

While various embodiments of the disclosed technology have been described above, it should be understood that they have been presented by way of example only, and not of limitation. Likewise, the various diagrams may depict an example architectural or other configuration for the disclosed technology, which is done to aid in understanding the features and functionality that can be included in the disclosed technology. The disclosed technology is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the technology disclosed herein. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

The invention claimed is:

1. A system for therapy management in a healthcare practice that includes multiple medical facilities a plurality of which are used by a patient who is undergoing a physical therapy program that has been prescribed by a physician of a medical facility of the healthcare practice for providing a recovery path of the patient, the multiple medical facilities providing different types of medical data, the system comprising:

a healthcare practice computing system comprising a server and a central data repository configured to receive and store clinical data associated with a plurality of identified patients from the multiple medical facilities of the healthcare practice, and to retrieve and provide the stored clinical data when accessed;

a first client computing device having a processor that is programmed in accordance with a physician-side physical therapy application to receive and store a prescription for the physical therapy program for the patient that includes a protocol of prescribed physical therapy exercises, to provide a code to the patient for downloading the prescribed physical therapy exercises, to download a patient-side physical therapy application, to identify the patient to the healthcare practice computing system upon receiving a log onto the healthcare practice computing system and the patient code by communicating with the central data repository and comparing the patient logging onto the healthcare practice computing system with a list of available patients, and upon successful patient logon and identification to the healthcare practice computing system, to retrieve the prescribed physical therapy exercises and download the patient-side physical therapy application and the prescribed protocol of physical therapy exercises to a patient client computing device;

a therapy product for use by the patient in performing the protocol of prescribed physical therapy exercises of the prescribed physical therapy program, the therapy product having a detection apparatus that senses motion of the patient to track performance by the patient of the physical therapy exercises, the detection apparatus communicating data representative of the sensed patient's motion;

the patient client computing device comprising a display, an input device, an output device, a processor, and a non-volatile memory in which is stored the patient-side physical therapy application that when run by the patient client computing device processor programs the patient client computing device processor to receive the sensed patient's motion data through the input device, the patient-side physical therapy application also programming the patient client computing device processor to compare the received sensed patient's motion data produced by the patient when performing prescribed physical therapy exercises to motion required by the prescribed physical therapy exercises and to provide determinations as to quality of the patient's performance of the prescribed physical therapy exercises based on the comparison including whether the patient has performed appropriate physical therapy exercises at appropriate intervals, performed a prescribed number of repetitions of the prescribed physical therapy exercises, and achieved a desired range of motion during performance of the prescribed physical therapy exercises, the patient-side physical therapy application also programming the patient client computing device processor to display the determinations of the quality of the patient's performance of the prescribed physical therapy exercises on the display of the patient client computing device and to communicate quality determinations outside the patient client computing device through the output device of the patient client computing device;

wherein the first client computing device is further programmed to obtain clinical data associated with the patient from the central data repository, and to receive from the patient client computing device the determinations of the patient's performance of the prescribed physical therapy exercises, and to analyze the obtained clinical data in view of the received determinations of the patient's performance for determining the patient's progress on the recovery path and for improving the patient's prescribed physical therapy program for the recovery path;

wherein the central repository receives the quality determinations from the output of the patient client computing device; and wherein the physician-side physical therapy application is further configured to program the processor of the first client computing device to provide an integrated view of performance of all active patients of prescribed physical therapy programs;

wherein the physician-side physical therapy application is further configured to program the processor of the first client computing device to provide an interactive view of a patient's clinical data on a display, wherein the programming permits a user to adjust a variable factor of the clinical data, and to see effects on the clinical data caused by the adjustment shown in the interactive view on the display; and wherein the physician-side physical therapy application programming of the processor of the first client computing device to provide the interactive view comprises displaying a graphical representation of a healthcare practice's profits as a function of a particular medical article provided to patients, wherein the programming permits the user to adjust data concerning usage of the particular medical article to see on the interactive display how the adjustment affects profits.

2. A system for therapy management in a healthcare practice that includes multiple medical facilities a plurality of which are used by a patient who is undergoing a physical therapy program that has been prescribed by a physician of a medical facility of the healthcare practice for providing a recovery path of the patient, the multiple medical facilities providing different types of medical data, the system comprising:

a healthcare practice computing system comprising a server and a central data repository configured to receive and store clinical data associated with a plurality of identified patients from the multiple medical facilities of the healthcare practice, and to retrieve and provide the stored clinical data when accessed;

a first client computing device having a processor that is programmed in accordance with a physician-side physical therapy application to receive and store a prescription for the physical therapy program for the patient that includes a protocol of prescribed physical therapy exercises, to provide a code to the patient for downloading the prescribed physical therapy exercises, to download a patient-side physical therapy application, to identify the patient to the healthcare practice computing system upon receiving a log onto the healthcare practice computing system and the patient code by communicating with the central data repository and comparing the patient logging onto the healthcare practice computing system with a list of available patients, and upon successful patient logon and identification to the healthcare practice computing system, to retrieve the prescribed physical therapy exercises and download the patient-side physical therapy application and the prescribed protocol of physical therapy exercises to a patient client computing device;

a therapy product for use by the patient in performing the protocol of prescribed physical therapy exercises of the prescribed physical therapy program, the therapy product having a detection apparatus that senses motion of the patient to track performance by the patient of the physical therapy exercises, the detection apparatus communicating data representative of the sensed patient's motion;

the patient client computing device comprising a display, an input device, an output device, a processor, and a non-volatile memory in which is stored the patient-side physical therapy application that when run by the patient client computing device processor programs the patient client computing device processor to receive the sensed patient's motion data through the input device, the patient-side physical therapy application also programming the patient client computing device processor to compare the received sensed patient's motion data produced by the patient when performing prescribed physical therapy exercises to motion required by the prescribed physical therapy exercises and to provide determinations as to quality of the patient's performance of the prescribed physical therapy exercises based on the comparison including whether the patient has performed appropriate physical therapy exercises at appropriate intervals, performed a prescribed number of repetitions of the prescribed physical therapy exercises, and achieved a desired range of motion during performance of the prescribed physical therapy exercises, the patient-side physical therapy application also programming the patient client computing device processor to display the determinations of the quality of the patient's performance of the prescribed physical therapy exercises on the display of the patient client computing device and to communicate quality determinations outside the patient client computing device through the output device of the patient client computing device;

wherein the first client computing device is further programmed to obtain clinical data associated with the patient from the central data repository, and to receive from the patient client computing device the determinations of the patient's performance of the prescribed physical therapy exercises, and to analyze the obtained clinical data in view of the received determinations of the patient's performance for determining the patient's progress on the recovery path and for improving the patient's prescribed physical therapy program for the recovery path;

wherein the central repository receives the quality determinations from the output of the patient client computing device; and wherein the physician-side physical therapy application is further configured to program the processor of the first client computing device to provide an integrated view of performance of all active patients of prescribed physical therapy programs;

wherein the physician-side physical therapy application is further configured to program the processor of the first client computing device to provide an interactive view of a patient's clinical data on a display, wherein the programming permits a user to adjust a variable factor of the clinical data, and to see effects on the clinical data caused by the adjustment shown in the interactive view on the display; and wherein the physician-side physical therapy application programming of the processor of the first client computing device to provide the interactive view comprises displaying a graphical representation of a healthcare practice's profits as a function of a particular medical article provided to patients, wherein the programming permits the user to adjust data concerning usage of the particular medical article to see on the interactive display how the adjustment affects profits; and wherein the physician-side physical therapy application programming of the processor of the first client computing device to provide the interactive view comprises displaying the graphical representation of the healthcare practice's profits as a function of a particular prescribed brace for patients, wherein the programming permits the user to adjust data concerning usage of the particular prescribed brace to see on the interactive display how the adjustment affects profits.

* * * * *